United States Patent [19]

Welker

[11] 4,440,032

[45] Apr. 3, 1984

[54] SAMPLER INCORPORATING A PURGE SYSTEM

[75] Inventor: Robert H. Welker, Sugar Land, Tex.

[73] Assignee: Welker Engineering Company, Sugar Land, Tex.

[21] Appl. No.: 366,846

[22] Filed: Apr. 9, 1982

[51] Int. Cl.³ ............................................. G01N 1/14
[52] U.S. Cl. ................................. 73/863.84; 73/864.34
[58] Field of Search ........... 73/863.84, 863.83, 864.34, 73/864.35; 137/860, 240

[56] References Cited

U.S. PATENT DOCUMENTS

| | | | |
|---|---|---|---|
| 3,266,321 | 8/1966 | Fenske et al. | 73/863.83 |
| 3,363,644 | 1/1968 | Malec | 137/860 X |
| 3,389,716 | 6/1968 | Wilburn | 137/240 |
| 3,945,770 | 3/1976 | Welker | 92/90 X |
| 4,237,935 | 12/1980 | Delmonte et al. | 137/860 |

OTHER PUBLICATIONS

Welker Engineering Company Publication G-1979.

*Primary Examiner*—S. Clement Swisher
*Assistant Examiner*—Tom Noland

[57] ABSTRACT

A crude oil sampling apparatus having a purge system as set forth in the preferred and illustrated embodiment. The sampling system includes an elongate probe which is driven by a diaphragm motor. This probe extends through a fixed housing and terminates at a sample collection head. The probe is provided with two passages through it. One passage is to remove the sample. As the probe is reciprocated, it captures sample and the sample is forced into the probe and along a passage therein past a check valve. The system includes a second passage opening into the first passage through a check valve. This is included to purge the probe and thereby empty or void the passage whereby all vestiges of a sample can be delivered from the equipment into a collection container or the like.

7 Claims, 3 Drawing Figures

SAMPLER INCORPORATING A PURGE SYSTEM

BACKGROUND OF THE DISCLOSURE

This apparatus relates to an improved pumping system. As set forth in U.S. Pat. No. 3,945,770 of the present inventor, a high pressure pump has been devised. The pump utilizes a solid, non-yielding reciprocating member and an opposing resilient plug. The plug has a dished area as set forth in that patent, and collapses on pressing the two components together. The relative squeeze forces any liquid captured in the dished area through a passage.

This apparatus has achieved some success as a sample gathering device. In the sale of chemicals flowing in a pipeline, including crude oil, the sales price is often determined by the quality of the product. To this end, a sample must be taken from the pipeline. It is fairly difficult to obtain a sample from a high pressure, high flow pipeline. Nevertheless, the apparatus constructed in accordance with the referenced patent has achieved admirable results in gathering samples.

A sample must ordinarily be separately captured in a container or bottle. It is normally unwise to comingle consecutive samples because they may very well mislead the following laboratory analysis. Moreover, it is helpful to isolate samples so that consecutive samples obtained from a sample collection apparatus may be properly tagged or labeled. For instance, one sample may be obtained from a first time period and the next sample from the same equipment may be collected over the next occurring time period. There is some chance of data distortion by leaving a portion of a collected sample in the tubing or conduit extending from the sample collection apparatus to a collection bottle. All of these problems can be overcome through the implementation of the present invention. The disclosed and claimed apparatus sets forth a sample collection system including a purge system. This contemplates the introduction of a purge gas behind a sample to separate it from the next sample. Moreover, it forces all of the volume of the sample from the lines and into the storage container. The purge gas can be introduced periodically to define consecutive samples. It can also be introduced through the system to assure that the entirety of sample material is collected in a single lot.

With the foregoing problems in view, one of the features of this apparatus is a sample purge system which can be periodically operated to clear a sample from the sample collection apparatus and to deliver the sample therefrom in a single lot or quantity. This assists in the storage and collection of the sample. Further, it does not interfere with the sample collection process, and is dormant until operated. The lack of interference enables the sample to be collected in the ordinary fashion, and also enables the downstream collection facility to clearly segregate different samples from following samples.

The purge system can be incorporated in a sampler pump having a piston reciprocating in a cylinder. The purge apparatus connected with the sampler again introduces the purge fluid behind the sample to assist in sample isolation.

BRIEF SUMMARY OF THE DISCLOSED AND ILLUSTRATED APPARATUS

A high pressure pumping apparatus is disclosed as support structure and incorporates a purge system therewith. This includes a chamber adapted to be filled with a fluid to be pumped. The chamber is defined between a solid and non-yielding reciprocating member and an opposing non-yielding member. A resilient plug is captured between the two members. There are opposing faces which are pulled apart, and one of the two opposing faces is dished out, thereby defining a high pressure pump chamber. A suitable motor such as a diaphragm drives an elongate rod which applies a compressive force to the opposing faces, including the resilient plug. The resilient plug shrinks as pressure is applied to it, first defining a surrounding seal adjacent to its captive chamber at the dished portion. The dished chamber area reduces in size under pressure to thereby force fluid from the chamber. A small passage communicates with the dished area and delivers fluid from it through a check valve. A check valve communicates with a passage in a reciprocating rod to remove the pressure produced sample. The reciprocating rod carries a second axial passage therealong, and this passage terminates through a check valve. When purge fluid is forced through this second axial passage and the check valve, it clears the outlet passage of any sample which is in the passage.

BRIEF DESCRIPTION OF THE DRAWINGS

So that the manner in which the above recited features, advantages and objects of the invention, as well as others, which will become apparent, are attained and can be understood in detail, a more particular description of the invention, briefly summarized above, may be had by reference to the embodiments thereof illustrated in the appended drawings, which drawings form a part of this specification. It is to be noted, however, that the appended drawings illustrate only typical embodiments of the invention and are not to be considered limiting of its scope, for the invention may admit to other equally effective embodiments.

DETAILED DESCRIPTION OF THE PREFERRED EMBODIMENT

Figure 1:
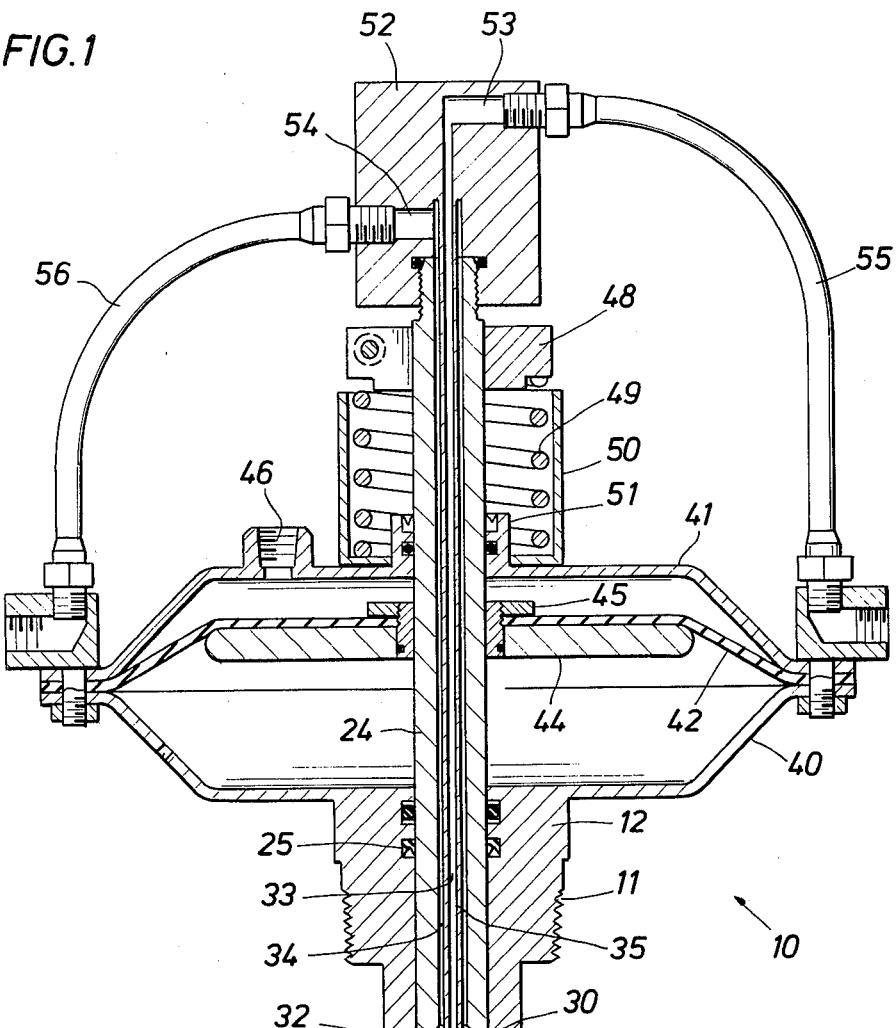
FIG. 1 is a sectional view through a crude oil sampler incorporating an elongate probe having an outlet passage for the sample and further disclosing a purge system with an inlet passage and check valve therefor.

Attention is first directed to FIG. 1 of the drawings. This shows, in sectional view, the entire structure of a fluid sample pump system. As will be developed, it also includes a purge system. The purge system is better understood after the development of certain background details regarding the pump system of FIG. 1, and the description will thus begin with the structure. The pump system of FIG. 1 is identified by the numeral 10. It includes an elongate probe or wand at the lower portions, and it is adapted to be positioned within a tank or to the surrounding pipeline at a set of threads 11 on a surrounding lower peripheral housing 12. The elongate wand includes a probe-like construction which is fixed to the thicker cylindrical body 12 supporting a tubular sleeve 13. The sleeve 13 has a number of ports or holes at 14 to introduce fluid from the tank or other container. Moreover, the sleeve 13 is fixedly joined at one end to the anchored cylindrical body portion 12 and threads to a bottom plug 15 at the opposite end. The bottom plug 15 fits within a small sleeve 16, the sleeve 16 being fastened around an upstanding cylindrical post and being held to it by means of a fastening pin 17 in a drilled hole. A resilient plug 18 is captured within the sleeve 16. It terminates at an encircling top lip 19 surrounding a dished cavity area 20. The resilient plug 18 works against a corresponding face 21, the face 21 reciprocating toward the dished cavity or chamber and sealing against the peripheral lip 19. When that seal is perfected, any fluid in the chamber is captured. The face 21, therefore, reciprocates by supporting structure as will be described into the area adjacent to the chamber 20 and seals. This operates the pump apparatus to capture any liquid that is in the chamber 20 when closure is effected.

The numeral 24 identifies an elongate reciprocating push rod. It is axially hollow. On the outer surface, it passes through a set of seals at 25 which prevent leakage along the shaft. The push rod terminates at an enlarged threaded spool 26, the spool 26 being threaded to the end of the push rod and incorporating the face 21. The face 21 is formed of unyielding material. The plug 18 is formed of resilient or yielding material. It is supported on an unyielding body. When the axial loading contemplated by this apparatus occurs, pumping action is initiated. The push rod 24 moves the face 21. Pumped fluid flows through the small passage 27 through the face 21. This passage terminates at an enlarged shoulder, and a check valve element 28 is forced against this shoulder by a coil spring 29. The check valve element comprises a pin with a surrounding lip or shoulder on it which plugs the passage 27. This prevents back flow out through the passage 27. The check valve element is forced into the check valve seat by the coil spring 29 which is captured below a plug having an axial passage 30. The passage 27 opens into a hollow fitting 31, the fitting having an escape passage at the top. This defines a check valve chamber. Fluid flow is, therefore, through this small passage 27, pass the check valve element 28 and into the chamber. Fluid flow escapes the chamber through the small opening 30. The hollow fitting 31 is captured on the interior of the internally threaded sleeve 26 and is held on the interior of a counter-bored chamber 32 at the lower end of the push rod 24.

The push rod is axially drilled. A hollow sleeve is fixedly positioned within it, the sleeve being identified at 35. This defines an internal flow path or passage 33. There is an external flow path 34. The external flow path communicates with the internal chamber 32, and this is the sample outlet path. In other words, sample is forced from the chamber 20 as that chamber vanishes under axial loading and flows through the passage 27, pass the check valve element 28, pass the spring 29 and to the exterior by means of the passage 30. The fluid continues to flow through the chamber 32 and into the lengthwise passage 34 on the interior of the push rod. This exterior passage extends upwardly along the full length of the push rod.

Figure 2:
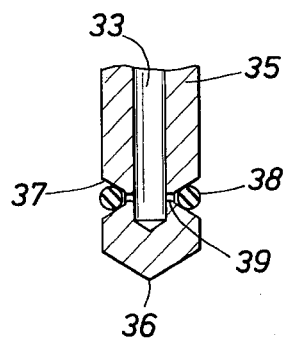
FIG. 2 is an enlarged sectional view showing a check valve construction through which purge fluid is introduced for purging in the apparatus shown in FIG. 1.

This flow path provides an outlet passage as will be described for the sample. It is on the exterior of an internal tubular sleeve 35. That divides and, therefore, sets up two passages, the central passage being identified by the numeral 33. It is concentric and on the interior. Perhaps it is understood better by referring to FIG. 2 of the drawings. There, the passage 33 extends downwardly. The surrounding wall which defines the two separate passages terminates at a transverse wall portion 36. The exterior is notched by forming an encircling groove 37. The groove serves as an undercut to receive and seat an O-ring 38. The O-ring is captured in the groove 37. At spaced locations, radial holes 39 are drilled through the wall so that the interior is communicated with the exterior. Flow in one direction only is permitted because the O-ring 38 functions as a check valve element. In other words, flow is from the interior to the exterior. As such flow occurs, it seeps out from beneath the O-ring. It cannot flow in the opposite direction because the O-ring prevents flow in that direction.

The equipment shown in FIG. 1 is reciprocated in operation. A fluid motor mechanism is included to accomplish this. It uses a diaphragm. To this end, it includes a lower diaphragm housing 40 parallel to and spaced from an upper diaphragm housing 41. The two terminate at an encircling lip or shoulder, and they are faced toward one another to capture, in a clamping arrangement, the peripheral edge of a diaphragm 42. The diaphragm 42 spans the chamber. The diaphragm 42 is a flexible member, either made of a resilient material or a relatively thin metallic diaphragm folded with circular pleats to enable flexure. The diaphragm is adjacent to a backing plate 44. The backing plate is drilled at the center and supports a hollow threaded clamp ring 45. The ring 45 surrounds the push rod 24 and joins to it, and has an overhanging lip or shoulder to clamp the diaphragm to prevent leakage along the push rod. This enables the fluid motor to reciprocate the push rod. To this end, the lower chamber can be evacuated to atmosphere by means of a small hole or passage. The upper chamber is hydraulically or pneumatically pressured by delivery of a fluid under pressure through the fitting 46.

In general, fluid under pressure is introduced to the topside of the diaphragm 42 forces it downwardly. The diaphragm is fixed to the fitting 45 which, in turn, is fixed to the push rod 24. The rod 24 is, therefore, reciprocated. When it reciprocates, it travels downwardly and operates the vanishing chamber pump construction shown in FIG. 1.

A collar 48 is clamped around the push rod. It has a downwardly facing shoulder which abuts a coil spring 49 captured within a cylindrical housing 50. The push rod 24 passes through the top housing member 41, and a surrounding upstanding collar 51 enclosing a set of seals enables the reciprocating push rod to slide through the collar without leakage. The coil spring 51 forces the housing 41 downwardly relative to the push rod 24. The collar 48 serves as a support for the coil spring 49 which forces the push rod 24 relatively upwardly. This collar is typically a split ring and is joined by a transverse bolt through two ends of the collar which clamps the collar and pulls it snug around the push rod. The push rod terminates with a set of threads. It is joined to a manifold block 52 by threaded connection. The manifold block 52 is drilled with a passage 53 which turns and connects with the passage 33 previously discussed. The thin wall member 35, having the form of a cylinder, extends from the manifold block 52 into the push rod. A radial passage 54 carries the sample away from the passage 34. The block 52 supports an inlet line 55 adapted to be connected through a fitting to a source of purge fluid. The lateral or radial passage 54 connects with a line 56 which is the sample outlet line. The lines 55 and 56 connect to suitable fittings including elbows, and they are conveniently anchored by bolts on the periphery of the diaphragm housing 41. The hoses 55 and 56 are flexible to accommodate reciprocating movement. Extra length is included for this.

In operation, the device functions in the following manner. It is mounted on a pipeline or tank to remove a sample. This is accomplished by locating a threaded opening in the pipeline and threading the threads 11 to that. This extends the lower portions of the sample collection apparatus into the fluid to be sampled. This anchors the diaphragm housing. The stroke is adjusted by adjusting the location of the collar 48. This collar and the spring below it are moved to define the beginning point of the push rod 24 prior to operation. The actual length of stroke is determined by the length of travel of the diaphragm 42. This movement is coupled to the push rod which, in turn, reciprocates components at the lower end as will be described. If a one inch stroke is required, fluid is introduced through the fitting 46 until the diaphragm has moved one inch. Moreover, this stroke is the stroke necessary to operate the pumping mechanism featuring a vanishing chamber pump.

It will be noted that the upper end of the push rod reciprocates and carries with it the manifold 52. The hoses 55 and 56 flex and bend to accommodate the stroke.

Crude oil and the like are pumped by closure of the solid unyielding member opposite the resilient plug 18. The plug 18 has a surrounding peripheral shoulder 19. Contact between the shoulder 19 and the opposing face isolates the chamber 20. The resilient member 18 is captured between a solid member below it and the reciprocating solid and unyielding member above it. It is squeezed, thereby distorting the chamber 20 which vanishes and forces the captured fluid through the passage 27. The passage 27 features a check valve 28, and pressure above a specified level is required to overcome the check valve. The flow of crude oil pass the check valve continues upwardly into the push rod. The flow path is upwardly and through the annual flow space 34. The space 34 is an outlet passage for the sample. Each reciprocation of the push rod forces another portion of sample into the passage 34. For instance, it may require twenty strokes to obtain a sample of requisite size. Each stroke forces the sample up through the passage 34.

One of the features of this apparatus is the purge system. Assume that an inert gas is used in the purge system. Assume that the necessary number of strokes to obtain a sample have occurred. At this time, it is wise to isolate the sample from the prior sample and from the succeeding sample. This isolation is achieved by use of the purge system. A purge procedure is initiated simply by introducing a purge fluid such as nitrogen through the line 55 at high pressure. It flows through the line 55 into the passage 53 and downwardly into the central passage 33. This is shown better in FIG. 2. The flow of purge fluid continues through the radial passage 39. This flow from beneath the resilient O-ring 38 expands the O-ring sufficiently to permit the purge fluid to escape the O-ring. The exit route for the purge fluid is then up through the passage 34, and it pushes the sample in front of it. The sample is expelled from the passage 34 and out through the conduit 56.

To place scale values on this procedure, assume that a sample of sufficient size is obtained by fifty strokes of the pump. Through use of a counter which counts the number of pressure pulses applied to the upper side of the diaphragm, fifty strokes can be counted. The fifty strokes will remove a sample of a requisite size. Thereafter, a purge fluid such as nitrogen gas is introduced through the conduit 55 for measured intervals, say thirty seconds. This will force all of the sample from the passage 34. Very little sample remains below the point of injection of purge fluid, and that portion of sample that is located in the annular passage 34 is forced out of the system. The sample is then collected by suitable means on flowing from the conduit 56.

Flow in the reverse direction is forbidden. It is not possible for sample to get into the passage 33, that passage being devoted exclusively to the introduction of purge fluid.

Figure 3:
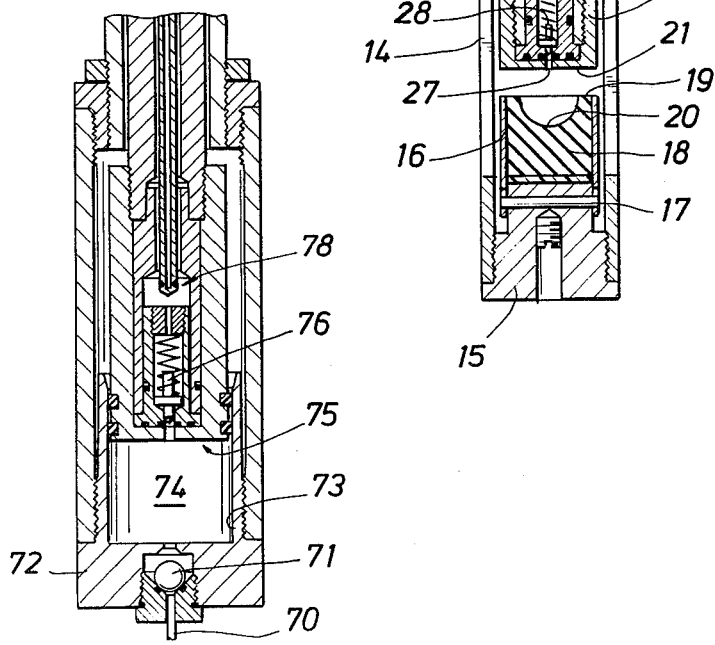
FIG. 3 is a sectional view of an alternate construction of a pump having a purge system.

FIG. 3 discloses an alternate form of sample collection apparatus featuring a purge system. The apparatus is similar to that shown in FIG. 1 except a nonresilient pumping element is included. The elongate wand includes an angular intake tube 70 delivering sample to a check valve 71 supported by a bottom plate 72. The plate 72 supports an upstanding shirt 73. This skirt defines a cylindrical, closed chamber 74 to receive sample into the chamber prior to pumping. A movable piston assembly 75, supporting a check valve 76, forces fluid into the valve 76. The pumping action is similar to FIG. 1 from this point, and the purge valve 78 operates in the same manner.

Many changes and alterations in scale of structure and materials can be included. However, the scope of the present disclosure is determined by the claims which follow.

I claim:
1. Sample collecting apparatus comprising:
(a) an elongate hollow body having the form of a rod and which body is adapted to have one end extended into a container having a volume of fluid therein to be sampled, said body having a second end remote from said one end;
(b) sample gathering means at the one end of said body for insertion into the fluid to be sampled;
(c) sample outlet passage means connected to said sample gathering means and extending therefrom along said rod to a sample outlet port for delivery of a sample;
(d) purge line means extending from an inlet near the second end toward said sample gathering means for introduction of a purge fluid into said sample outlet passage means;
(e) selectively operable valve means for controlling operation of said purge line means into said sample outlet passage means to control flow of a purge fluid into said sample outlet passage means;
(f) wherein said purge line means extends along said elongate hollow body and terminates at a check valve means comprising said selectively operable valve means;
(g) wherein said sample outlet passage means and purge line means are coterminous at said one end connected together through said selectively operable valve means; and
(h) wherein said sample outlet passage means and said purge line means comprise first and second elongate hollow conduits, the second within the first, the second being the purge line conduit and of thin wall construction and having a closed end with a passage through the wall thereof, and said selectively operable valve means comprises a means selectively closing said passage through said wall.

2. The apparatus of claim 1 wherein said elongate hollow body comprises a hollow push rod with two passages therein; said two passages comprising said first and second elongate hollow conduits, and
- a fitting adapted to be connected with the container having the volume of fluid therein to be sampled, said fitting having a passage with cooperative seal means therethrough to permit said elongate push rod to be reciprocated therethrough.

3. The apparatus of claim 1 wherein said elongate hollow body is connected to a reciprocating motor means imparting reciprocating motion thereto for operation of said sample gathering means to deliver fluid from the container into said sample outlet passage means.

4. The apparatus of claim 1 wherein said wall is notched to receive and hold a resilient O-ring therein and said passage is formed adjacent said O-ring which O-ring functions as a check valve in blocking and opening said passage, said notched wall, O-ring, and said passage comprising said check valve means.

5. The apparatus of claim 4, including a purge fluid supply line connected near the second end of said elongate hollow body and flows through a passage along said elongate hollow body which passage comprises said purge line means.

6. The apparatus of claim 1 wherein said sample gathering means comprises:
- a resilient body having a dished area for sealing around the dished area against a confronting face to isolate sample in the dished area; and
- means forcing said resilient body toward said confronting face to pressurize sample.

7. The apparatus of claim 1 wherein said sample gathering means comprises a solid piston in a cylinder, and means admitting sample into said cylinder to be pressurized by movement of said piston.

* * * * *